(12) United States Patent
Bruun

(10) Patent No.: US 10,695,292 B2
(45) Date of Patent: Jun. 30, 2020

(54) CHEWING GUM COMPOSITION FOR USE IN ALLEVIATION OF XEROSTOMIA INDUCED BY RADIOTHERAPY TREATMENT

(71) Applicant: Fertin Pharma A/S, Vejle (DK)

(72) Inventor: Heidi Ziegler Bruun, Vejle Ø (DK)

(73) Assignee: Fertin Pharma A/S, Vejle (DK)

( * ) Notice: Subject to any disclaimer, the term of this patent is extended or adjusted under 35 U.S.C. 154(b) by 0 days.

(21) Appl. No.: 15/735,723

(22) PCT Filed: Jun. 23, 2016

(86) PCT No.: PCT/EP2016/064578
§ 371 (c)(1),
(2) Date: Dec. 12, 2017

(87) PCT Pub. No.: WO2016/207299
PCT Pub. Date: Dec. 29, 2016

(65) Prior Publication Data
US 2019/0060228 A1    Feb. 28, 2019

(30) Foreign Application Priority Data

Jun. 23, 2015  (WO) ................ PCT/EP2015/064074

(51) Int. Cl.
| A61K 9/68 | (2006.01) |
| A61K 47/30 | (2006.01) |
| A61K 47/26 | (2006.01) |
| A61K 47/24 | (2006.01) |
| A61K 33/16 | (2006.01) |
| A61K 47/02 | (2006.01) |
| A61P 1/00 | (2006.01) |

(52) U.S. Cl.
CPC ............ *A61K 9/0058* (2013.01); *A61K 33/16* (2013.01); *A61K 47/02* (2013.01); *A61K 47/24* (2013.01); *A61K 47/26* (2013.01); *A61K 47/30* (2013.01); *A61P 1/00* (2018.01)

(58) Field of Classification Search
None
See application file for complete search history.

(56) References Cited

U.S. PATENT DOCUMENTS

| 4,241,090 | A | * | 12/1980 | Stroz | ........................ | A23G 4/06 |
| | | | | | | 426/4 |
| 4,906,455 | A | * | 3/1990 | Hoerman | ............. | A61K 9/0058 |
| | | | | | | 424/48 |
| 5,474,787 | A | * | 12/1995 | Grey | ...................... | A23G 4/066 |
| | | | | | | 426/3 |
| 5,702,687 | A | * | 12/1997 | Miskewitz | ................ | A61K 8/11 |
| | | | | | | 424/440 |
| 7,871,650 | B2 | * | 1/2011 | Sozzi | ....................... | A23G 4/06 |
| | | | | | | 426/3 |
| 9,420,806 | B2 | * | 8/2016 | Andersen | .................. | A23G 4/06 |
| 2003/0185884 | A1 | * | 10/2003 | Singh | .................... | A61K 9/0056 |
| | | | | | | 424/465 |
| 2004/0028772 | A1 | * | 2/2004 | Andersen | .................. | A23G 4/02 |
| | | | | | | 426/3 |
| 2004/0115305 | A1 | | 6/2004 | Andersen et al. | | |
| 2007/0196447 | A1 | * | 8/2007 | Weg | ...................... | A61K 9/0053 |
| | | | | | | 424/440 |

FOREIGN PATENT DOCUMENTS

| EP | 1 946 751 A1 | 7/2008 | |
| WO | WO 89/09594 A1 | 10/1989 | |
| WO | WO-2004004480 A1 * | 1/2004 | ............ A23G 3/004 |
| WO | WO 2010/135736 A2 | 11/2010 | |

OTHER PUBLICATIONS

A. N. Davies, "A comparison of artificial saliva and chewing gum in the management of xerostomia in patients with advanced cancer," Palliative Medicine 2000; 14: 197-203. (Year: 2000).*
Michael Edgar, Colin Dawes & Denis O'Mullane. Saliva and oral health an essential overview for the health professional fourth edition, Published by Stephen Hancocks Limited, 2012 (Year: 2012).*
Deasy, J.O. et al.; "Radiotherapy dose-volume effects on salivary gland function"; International Journal of Radiation Oncology—Biology—Physics, vol. 76, No. 3; Mar. 1, 2010; pp. S58-S63.
Dirix, P. et al.; "The influence of xerostomia after radiotherapy on quality of life: results of a questionnaire in head and neck cancer"; Support Care Cancer, vol. 16; Feb. 1, 2008; pp. 171-179.
Dost, F. et al.; "Stimulating the discussion on saliva substitutes: a clinical perspective"; Australian Dental Journal, vol. 58; Mar. 1, 2013; pp. 11-17.
Flink, H. et al.; "Influence of the time of measurement of unstimulated human whole saliva on the diagnosis of hyposalivation"; Archives of Oral Biology, vol. 50; Jun. 1, 2005; pp. 553-559.
Furness, S. et al.; "Interventions for the management of dry mouth: non-pharmacological interventions"; Cochrane Database of Systematic Reviews; Jan. 1, 2013; 52 pages.
Jellema, A.P. et al.; "Does radiation dose to the salivary glands and oral cavity predict patient-rated xerostomia and sticky saliva in head and neck cancer patients treated treated with curative radio therapy?"; Radiotherapy and Oncology, vol. 77; Nov. 1, 2005; pp. 164-171.
Jensen, A.B. et al.; "Influence of late side-effects upon daily life after radiotherapy for laryngeal and pharyngeal cancer"; Acta Oncolica, vol. 33; Jan. 1, 1994; pp. 487-491.

(Continued)

*Primary Examiner* — Michael P Cohen
(74) *Attorney, Agent, or Firm* — Lee & Hayes, P.C.

(57) ABSTRACT

The invention relates to a chewing gum composition for use in the alleviation of xerostomia induced by radiotherapy treatment, where the chewing gum composition comprises gum base and substantially no flavour ingredients. Moreover, the invention also relates to a dosage regimen for administering the chewing gum composition for use in alleviation of xerostomia induced by radiotherapy treatment. So in one embodiment of the invention the chewing gum composition is administered to a human subject before and/or during and/or after radiotherapy treatment.

22 Claims, 3 Drawing Sheets

(56) References Cited

OTHER PUBLICATIONS

Jensen, K. et al.; "A cross sectional quality of life study of 116 recurrence free head and neck cancer patients. The first use of EORTC H&5 N35 in Danish"; Acta Oncolgica, vol. 45; Jan. 1, 2006; pp. 28-37.

Mira, J.G. et al.; "Correlation between initial salivary flow rate and radiation dose in the production of xerostomia"; Acta Radiologica: Oncology, vol. 21, No. 3; Jan. 1, 1982; pp. 151-154.

Mortensen, H.R. et al.; "Prevalence and peak incidence of acute and late normal tissue morbidity in the DAHANCA 6&7 randomised trial with accelerated radiotherapy for head and neck cancer"; Apr. 1, 2012; pp. 69-75.

Navazesh, M. et al.; "Measuring salivary flow: challenges and opportunities"; The Journal of the American Dental Association, vol. 139; May 1, 2008; pp. 35s-40s.

Nieuw, A. et al.; "Current therapies for xerostomia and salivary gland hypofunction associated with cancer therapies"; Supportive Care in Cancer, vol. 11; Apr. 1, 2003; pp. 226-231.

Porter, S.R. et al.; "Xerostomia in head and neck malignancy"; Oral Oncology, vol. 46; Apr. 2010; pp. 460-463.

Wolff, M. et al.; "Oral mucosal wetness in hypo- and normosalivators"; Archives of Oral Biology, vol. 43; Jun. 1, 1998; pp. 455-462.

International Search Report dated Aug. 22, 2016 for International Application No. PCT/EP2016/064578.

Written Opinion dated Aug. 22, 2016 for International Application No. PCT/EP2016/064578.

\* cited by examiner

CHEWING GUM COMPOSITION FOR USE IN ALLEVIATION OF XEROSTOMIA INDUCED BY RADIOTHERAPY TREATMENT

This application claims the benefit under 35 U.S.C. § 371 of International Application No. PCT/EP2016/064578, filed Jun. 23, 2016, which claims the benefit of International Patent Application No. PCT/EP2015/064074, filed Jun. 23, 2015; which are incorporated by reference herein in their entirety.

FIELD OF THE INVENTION

The present invention relates to a chewing gum composition for use in the alleviation of xerostomia induced by radiotherapy treatment where the chewing gum composition comprises gum base and substantially no flavour ingredients.

BACKGROUND

Radiation induced xerostomia is a common side-effect when treating head and neck cancer during and after therapy (Mira J G, Fullerton G D, Wescott W B. Correlation between initial salivary flow rate and radiation dose in the production of xerostomia. Acta Radiol Oncol. 1982;21:151-4, Jellema A P, Doornaert P, Slotman B J, Leemans C R, Langendijk J A. Does radiation dose to the salivary glands and oral cavity predict patient-rated xerostomia and sticky saliva in head and neck cancer patients treated with curative radiotherapy? Radiother Oncol. 2005;77:164-71, Porter S R, Fedele S, Habbab K M. Xerostomia in head and neck malignancy. Oral Oncol. 2010;46:460-3). Xerostomia is the subjective feeling of oral dryness, whereas hyposalivation is the physiological reduction in salivary flow (Nieuw Amerongen A V, Veerman E C. Current therapies for xerostomia and salivary gland hypofunction associated with cancer therapies. Support Care Cancer. 2003;11:226-31). Hyposalivation is defined as unstimulated whole saliva flow of ≤0.2 mL/min. Very low saliva flow below 0.1 mL/min is part of the criteria for diagnosing Sjögren's syndrome. Symptoms of xerostomia become evident when saliva flow is about 0.1-0.2 mL/min (Wolff M, Kleinberg I. Oral mucosal wetness in hypo- and normosalivators. Arch Oral Biol. 1998;43:455-62, Flink H, Tegelberg A, Lagerlof F. Influence of the time of measurement of unstimulated human whole saliva on the diagnosis of hyposalivation. Arch Oral Biol. 2005;50:553-9). In healthy individuals, 0.5-1.5 L of saliva is produced daily. Saliva is secreted by the three paired major salivary glands and consists of approximately 99% water and 1% proteins and salt (Navazesh M, Kumar S K. Measuring salivary flow: challenges and opportunities. J Am Dent Assoc. 2008;139 Suppl:35s-40s). Normal daily secretion of saliva is vital for maintaining good oral health, nutrition intake and communication skills (Navazesh M, Kumar S K. Measuring salivary flow: challenges and opportunities. J Am Dent Assoc. 2008;139 Suppl:35s-40s).

The occurrence of radiation induced xerostomia can be illustrated with data from the Danish Head and Neck Cancer Group's database (DAHANCA). From January 2000 to December 2012, 1238 head and neck cancer patients from Odense University Hospital were scored by an observer-based system regarding xerostomia. The higher the score, the more profound the symptoms of xerostomia were. FIG. 1 illustrates how 45% of all patients coming to their first follow-up visit two to five months after finishing radiation therapy suffered from a slight degree of xerostomia (score 1). Thirty-one percent suffered from severe xerostomia (score 2 and 3). All DAHANCA xerostomia scores were rated by the treating physician.

Xerostomia is not necessarily associated with a significant reduction in salivary flow, but can merely be defined according to the symptoms presented by patient. To assess the severity of xerostomia in the clinic, a good approach is to make use of an observer-based system (e.g. the DAHANCA follow-up scoring system) along with a validated QOL measurement device (e.g. the EORTC H&N35 questionnaire) and salivary measurement (Deasy J O, Moiseenko V, Marks L, Chao K S, Nam J, Eisbruch A. Radiotherapy dose-volume effects on salivary gland function. Int J Radiat Oncol Biol Phys. 2010;76:S58-63).

Radiation causes a deficiency in saliva production and thickens the composition of saliva due to irradiation of the saliva glands. Radiotherapy may result in eating difficulties and unintended weight loss, dysphagia, dysgeusia, difficulties speaking, disturbed sleep, and general oral discomfort (Dost F, Farah C S. Stimulating the discussion on saliva substitutes: a clinical perspective. Aust Dent J. 2013;58:11-7, Furness S, Bryan G, McMillan R, Birchenough S, Worthington Helen V. Interventions for the management of dry mouth: non-pharmacological interventions. Cochrane Database of Systematic Reviews [Internet]. 2013; (9). Available: http://onlinelibrary.wiley.com/doi/10.1002/14651858.CD009603.pub3/abstract, Jensen A B, Hansen O, Jorgensen K, Bastholt L. Influence of late side-effects upon daily life after radiotherapy for laryngeal and pharyngeal cancer. Acta Oncol. 1994;33:487-91). The severity of xerostomia is affected by the total dose of radiation and is often irreversible (Jensen A B, Hansen O, Jorgensen K, Bastholt L. Influence of late side-effects upon daily life after radiotherapy for laryngeal and pharyngeal cancer. Acta Oncol. 1994;33:487-91, Mortensen H R, Overgaard J, Specht L, Overgaard M, Johansen J, Evensen J F, et al. Prevalence and peak incidence of acute and late normal tissue morbidity in the DAHANCA 6&7 randomised trial with accelerated radiotherapy for head and neck cancer. Radiother Oncol. 2012;103:69-75). Quality of life may become compromised and social activities limited. Various treatments are available to relieve the discomfort of xerostomia, including symptomatic relief by oral lubricants and saliva substitutes. Salivary stimulants may be considered where residual salivary gland function remains (Dirix P, Nuyts S, Vander Poorten V, Delaere P, Van den Bogaert W. The influence of xerostomia after radiotherapy on quality of life: results of a questionnaire in head and neck cancer. Support Care Cancer. 2008; 16:171-9).

Object and Summary of the Invention

It is an object of the present invention to provide a chewing gum composition for use in the alleviation of xerostomia induced by radiotherapy treatment, the chewing gum composition comprises gum base and substantially no flavour ingredients.

It has surprisingly been found that it is possible to relieve the discomfort of xerostomia in patients that have been subjected to radiotherapy treatment. The flow of saliva is increased and the composition of the saliva becomes less thick after using the chewing gum composition according to the present invention.

Moreover, the invention also relates to a dosage regimen for administering the chewing gum composition for use in alleviation of xerostomia induced by radiotherapy treatment. So in one embodiment of the invention the chewing gum composition is administered to a human subject before and/or during and/or after radiotherapy treatment.

BRIEF DESCRIPTION OF THE DRAWINGS

In the following, preferred embodiments of the invention will be described referring to the figures, where.

DESCRIPTION OF PREFERRED EMBODIMENTS/DETAILED DESCRIPTION

With the present invention, as described in the following, a chewing gum composition for use in the alleviation of xerostomia induced by radiotherapy treatment is provided where chewing gum composition comprises a gum base and substantially no flavour ingredients.

For head and neck cancer patients it is a challenge to find suitable products to increase salivary flow. After finishing radiotherapy the oral cavity is highly sensitive due to decreased salivary flow rate, thicker saliva, and alterations to the sense of taste. Sugar may contribute to or worsen xerostomia and increases the risk of carries and sweetness can also cause nausea. The chewing muscles are restrained because of radiation sequela and often confined to processing small food items.

It is known that chewing gum with flavours stimulate saliva flow in normal healthy people, and a skilled person would therefore expect—based on common knowledge—that a chewing gum composition for increasing saliva flow should comprise substantial amounts of flavour in order to stimulate saliva flow regardless users. Even when the users are head and neck cancer patients a skilled person would assume that the chewing gum composition should comprise flavours since flavours are known to stimulate saliva flow. This despite the knowledge that strong flavours are not favoured in the early phase of recovery as a lot of intake taste of metal. A skilled person would therefore not expect that a chewing gum composition without flavours would result in increased saliva flow in the order of more than 20% compared to unstimulated saliva flow. So that the presently claimed chewing gum composition with substantially no flavour ingredients actually increase saliva flow is surprising since the same increase in saliva flow compared to unstimulated saliva flow is not seen in the control group of healthy people.

Figure 1:
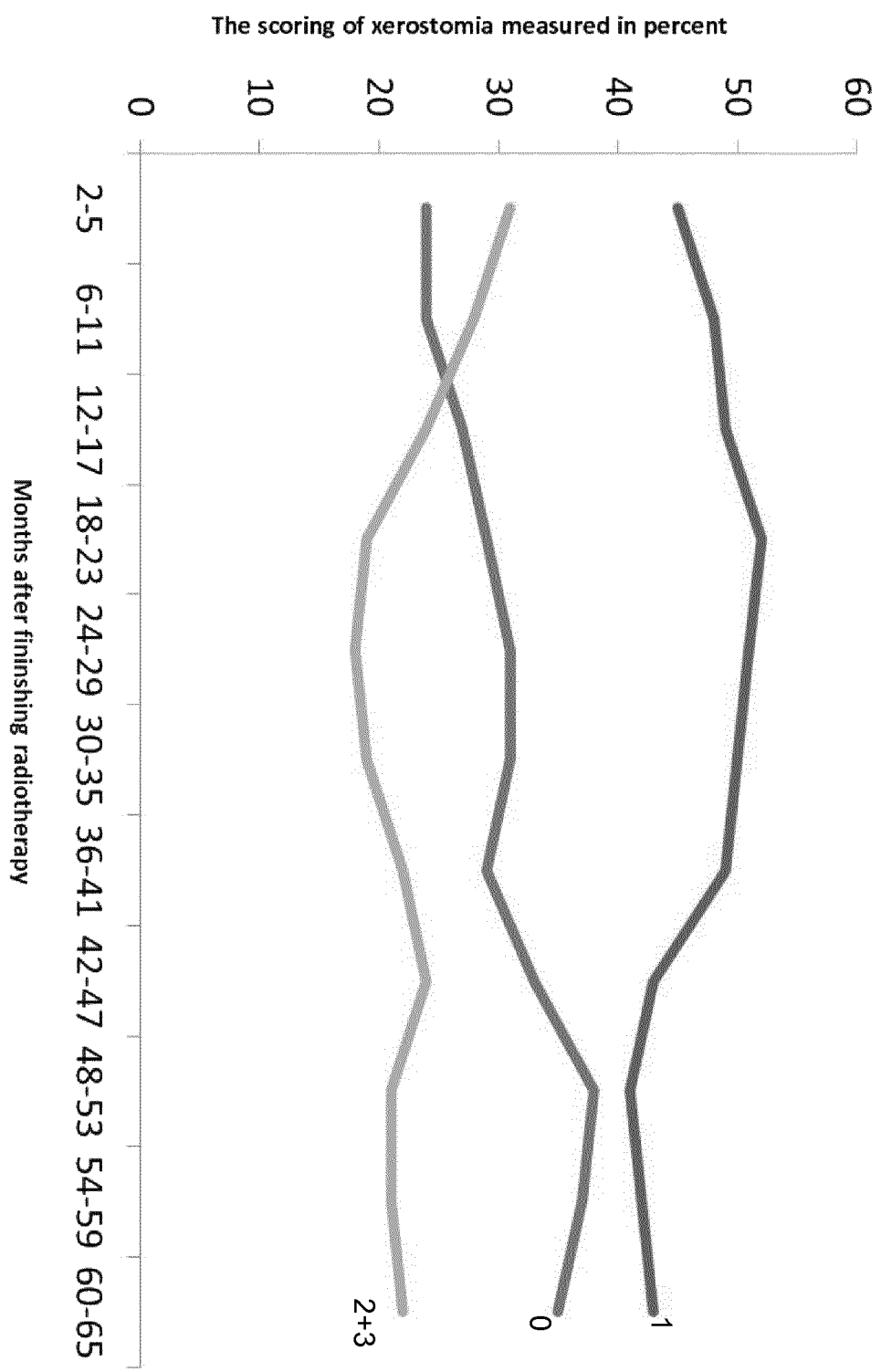
FIG. 1 shows the prevalence and scoring of xerostomia in Danish head and neck cancer patients from January 2000 to December 2012. All data are retrieved from DAHANCA's database. 0 represents xerostomia rated as "None" (score 0), and the 1 represents xerostomia rated as "Slight" (score 1). 2+3 represents the grouping of xerostomia rated as "Moderate" or "Severe" (score 2 and 3).

FIG. 1 shows that xerostomia is a frequent manifestation after primary treatment of head and neck cancers throughout 5 years of follow-up. The prevalence of xerostomia may still increase until 1 year after finishing treatment, as the damage inflicted upon the salivary glands take months to develop. Xerostomia may diminish throughout the period, and a certain decline from severe to slight xerostomia is seen after one year. The figure illustrates that over time, xerostomia may diminish in severity, but it remains a persistent late side-effect. Xerostomia is not a life threatening complication, but decreased saliva flow and changes in saliva composition are straining. Saliva often becomes sticky and unmanageable which compromises oral well-being and results in eating difficulties, increased risk of caries, and impaired speaking abilities. Interrupted sleep patterns due to dry mouth is also common. Living with xerostomia may inflict emotionally strain (worry, tension, and depression) and limit social activities.

In one embodiment of the invention, the chewing gum composition is a non-medical chewing gum which does not comprise an active medical ingredient.

In one embodiment of the invention, the chewing gum composition is a non-medical chewing gum which does not comprise a therapeutic agent.

In one embodiment of the invention, the chewing gum composition is a non-medical chewing gum meaning that the chewing gum does not comprise a medicament.

In one embodiment of the invention, more than 10% increase in salivary flow (g/ml) compared to unstimulated saliva flow is seen. In one embodiment more than a 20% increase in salivary flow compared to unstimulated saliva flow is seen. In one embodiment more than 30% increase in salivary flow compared to unstimulated saliva flow is seen.

In one embodiment of the invention a decreased viscosity of the saliva in the oral cavity is seen compared to unstimulated saliva. The saliva of the test subjects are more fluent after chewing on the chewing gum according to the present invention, which benefits the patients oral well-being as this patient group has a tendency to have thick and sticky saliva.

By the present invention, salivary secretion is increased for patients suffering from radiation induced xerostomia compared to persons that have not been subjected to radiation therapy. This was highly surprising and not expected by the present inventors. By means of the chewing gum according to the present invention, applicant showed with the presented study that the chewing gum was able to stimulate and increase the mean salivary output for twenty consecutive participants. This study confirmed that tasteless (86% of the test subjects liked the taste), soft (71% of the test subjects liked the texture), juicy (88% of the test subjects like the juiciness) chewing gum was able to stimulate the remaining function of residual salivary glands into increasing the saliva flow, and contributed to a positive altering in xerostomia and improved oral well-being reported by the patients.

By alleviation is meant to make e.g. pain or annoying symptoms less intense or more bearable.

By radiotherapy treatment is meant radiation therapy or radiotherapy, often abbreviated RT, RTx, or XRT, which is therapy using ionizing radiation, generally as part of cancer treatment to control or kill malignant cells.

As used herein, by the phrase "chewing gum" is meant any chewing gum such as extruded chewing gum, centre-filled chewing gum, or compressed chewing gum, slabs or sticks.

By the terms "gum base" and "gum base matrix" is meant the mainly water-insoluble and hydrophobic gum base ingredients that are mixed together before the bulk portion of the chewing gum is added. The gum base is the masticatory substance of the chewing gum which imparts most of the chew characteristics of the chewing gum. The gum base portion is retained in the mouth throughout the chew.

The term "bulk portion" intends to mean the mainly water-soluble and hydrophilic chewing gum ingredients that may be mixed into the gum base matrix after it has been made.

The term "weight of the chewing gum" or similar wording meaning the same is defined in the present context as weight of the chewing gum, not including the weight of an outer coating, such as a film coating and the like.

By the phrase "texture" is meant a qualitative measure of the visco-elastic properties of the chewing gum and of the overall mouth-feel experienced by the user during the chewing process. Thus the term "texture" encompasses measurable quantities such as hardness and elasticity as well as more subjective parameters related to the chew-feel experienced by a user.

The formulation of gum bases can vary depending on the particular product to be prepared and on the desired masticatory and other sensory characteristics of the final product. However, ranges (percent by weight) of the gum base components according to the present invention are: 5 to 40 percent by weight elastomeric compounds, 8 to 45 percent by weight natural resins (elastomer plasticizer), 5 to 50 percent by weight synthetic resins (elastomer plasticizer).

In addition, ranges (percent by weight) of the gum base components are 0 to 40 percent by weight waxes, 5 to 35 percent by weight softener other than waxes, 0 to 50 percent by weight filler, and 0 to 5 percent by weight of miscellaneous ingredients such as antioxidants, colorants, etc.

Elastomers provide the rubbery, cohesive nature to the gum, which varies depending on this ingredient's chemical structure and how it may be compounded with other ingredients. Elastomers suitable for use in the gum base and gum of the present invention may include natural or synthetic types. The elastomer compounds may be of natural origin but are preferably of synthetic origin, preferably synthetic polyesters.

Elastomer plasticizers vary the firmness of the gum base. Their specificity on elastomer inter-molecular chain interaction (plasticizing) along with their varying softening points cause varying degrees of finished gum firmness and compatibility when used in gum base. This may be important if it is desired to provide more elastomeric chain exposure to the alkane chains of the waxes.

The elastomer may be any water-insoluble polymer known in the art, and includes those gum polymers utilized for chewing gums and bubble gums. Illustrative examples of suitable polymers in gum bases include both natural and synthetic elastomers. For example, those polymers which are suitable in gum bases include, without limitation, natural substances (of vegetable origin) such as chicle gum, natural rubber, crown gum, nispero, rosidinha, jelutong, perillo, niger gutta, tunu, balata, guttapercha, lechi capsi, sorva, gutta kay, and the like, and mixtures thereof. Examples of synthetic elastomers include, without limitation, styrene-butadiene copolymers (SBR), polyisobutylene, isobutylene-isoprene copolymers, polyethylene, polyvinyl acetate and the like, and mixtures thereof.

Natural resins may be used according to the invention and may be natural rosin esters, often referred to as ester gums including as examples glycerol esters of partially hydrogenated rosins, glycerol esters of polymerised rosins, glycerol esters of partially dimerized rosins, glycerol esters of tally oil rosins, pentaerythritol esters of partially hydrogenated rosins, methyl esters of rosins, partially hydrogenated methyl esters of rosins, pentaerythritol esters of rosins, synthetic resins such as terpene resins derived from alpha-pinene, beta-pinene, and/or d-limonene, and natural terpene resins and combinations thereof.

In an embodiment of the invention, the resin comprises terpene resins, e.g. derived from alpha-pinene, beta-pinene, and/or d-limonene, natural terpene resins, glycerol esters of gum rosins, tall oil rosins, wood rosins or other derivatives thereof such as glycerol esters of partially hydrogenated rosins, glycerol esters of polymerized rosins, glycerol esters of partially dimerised rosins, pentaerythritol esters of partially hydrogenated rosins, methyl esters of rosins, partially hydrogenated methyl esters of rosins or pentaerythritol esters of rosins and combinations thereof.

Examples of generally non-biodegradable synthetic resins include polyvinyl acetate, vinyl acetate-vinyl laurate copolymers and mixtures thereof. Examples of nonbiodegradable synthetic elastomers include, but are not limited to, synthetic elastomers listed in Food and Drug Administration, CFR, Title 21, Section 172,615, Masticatory Substances, Synthetic specification, such as polyisobutylene. e.g. having a gel permeation chromatography (GPC) average molecular weight in the range of about 10,000 to 1,000,000 including the range of 50,000 to 80,000, isobutylene- isoprene copolymer (butyl elastomer), styrene-butadiene copolymers e.g. having styrene-butadiene ratios of about 1:3 to 3:1, polyvinyl acetate (PVA), e.g. having a GPC average molecular weight in the range of 2,000 to 90,000 such as the range of 3,000 to 80,000 including the range of 30,000 to 50,000, where the higher molecular weight polyvinyl acetates are typically used in bubble gum base, polyisoprene, polyethylene, vinyl acetate-vinyl laurate copolymer e.g. having a vinyl laurate content of about 5 to 50 percent by weight such as 10 to 45 percent by weight of the copolymer, and combinations hereof.

A gum base formulation may, in accordance with the present invention, comprise one or more softening agents. As used herein the term "softener" designates an ingredient, which softens the gum base or chewing gum composition and encompasses waxes, fats, oils, emulsifiers, surfactants and solubilisers.

The softening agent can be selected from: sucrose esters, tallow, hydrogenated tallow, hydrogenated and partially hydrogenated vegetable oils, cocoa butter, degreased cocoa powder, glycerol monostearate, glyceryl triacetate, lecithin, mono-, di- and triglycerides, acetylated monoglycerides, lanolin, sodium stearate, potassium stearate, glyceryl lecithin, propylene glycol monostearate, glycerine, fatty acids (e.g. stearic, palmitic, oleic and linoleic acids) and combinations thereof.

To soften the gum base further and to provide it with water-binding properties, which reduce its adhesive properties, one or more emulsifiers can be added to the composition. Useful emulsifiers can include, but are not limited to, the group of cyclodextrins, polyoxyethylene castor oil derivatives, polyoxyethylene alkyl ethers, macrogol alkyl ethers, block copolymers of ethylene and propylene oxides, polyoxyethylene alkyl ethers, polyoxyethylene glycols, polyoxyethylene sorbitan fatty acid esters, polyoxyethylene (20) sorbitan monostearates, polyoxyethylene (20) sorbitan monooleates, polyoxyethylene stearates, sobitan esters, diacetyl tartaric ester of monoglycerides, lactylated monoglycerides, glyceryl monostearate, propylene glycol monostearate, mono- and diglycerides of edible fatty acids, lactic acid esters and acetic acid esters of mono- and diglycerides of edible fatty acids, acetylated mono and diglycerides, sugar esters of edible fatty acids, Na-, K-, Mg- and Ca-stearates, lecithin, hydroxylated lecithin and the like and mixtures thereof are examples of conventionally used emulsifiers which can be added to the chewing gum base. In one embodiment of the invention, emulsifiers are used in an amount of 0 to 18 percent by weight, preferably 0 to 12 percent by weight of the gum base.

Waxes and fats are conventionally used for the adjustment of the texture and for softening of the chewing gum base when preparing chewing gum bases. In connection with the present invention, any conventionally used and suitable type of natural and synthetic wax and fat may be used, such as for instance rice bran wax, polyethylene wax, petroleum wax (refined paraffin and microcrystalline wax), sorbitan monostearate, tallow, propylene glycol, paraffin, beeswax, carnauba wax, candelilla wax, cocoa butter, degreased cocoa powder and any suitable oil or fat, as e.g. completely or partially hydrogenated vegetable oils or completely or partially hydrogenated animal fats.

The chewing gum base may include one or more fillers/texturisers including as examples, magnesium and calcium carbonate, sodium sulphate, ground limestone, silicate compounds such as magnesium and aluminum silicate, kaolin and clay, aluminum oxide, silicium oxide, talc, titanium oxide, mono-, di- and tri-calcium phosphates, cellulose polymers, such as wood, and combinations thereof. In an embodiment of the invention, said chewing gum comprises a biodegradable gum base polymer.

In one embodiment the chewing gum composition does not comprise any additional filler than the filler in the gum base. So in one embodiment the chewing gum composition comprises an inorganic mineral filler in the amount of less than 25%, or less than 20%, or less than 10%, or less than 5% by weight of the chewing gum composition. In one embodiment the chewing gum composition comprises calcium carbonate in the amount of less than 25%, or less than 20%, or less than 10%, or less than 5% by weight of the chewing gum composition. Regular chewing gum tablets often have a high amount of filler such as calcium carbonate but for this specific patient group it is important that the product isn't dry or sense dry for the patient as the chewing gum should stimulate the saliva production by chewing and release some moist effect into the oral cavity. Therefor it is important that the product don't absorb any saliva.

The chewing gum base may include miscellaneous ingredients such as antioxidants, colorants, dry-binders, tableting aids, anti-caking agents, enhancers, absorption enhancers, buffers, active ingredients, water-soluble indigestible polysaccharides, water-insoluble polysaccharides or any combination thereof.

Antioxidants prolong shelf life and storage of gum base, finished gum or their respective components including fats and flavour oils. Antioxidants suitable for use in gum base include butylated hydroxyanisole (BHA), butylated hydroxytoluene (BHT), betacarotenes, tocopherols, acidulants such as Vitamin C, propyl gallate, other synthetic and natural types or mixtures thereof. In some embodiments, one or more colors can be included in the chewing gum.

The amount of gum base in the chewing gum composition according to the present invention is high compared to chewing gums known in the art. In one embodiment the chewing gum composition comprises from 25 to 80% by weight of gum base. In one embodiment the chewing gum composition comprises from 60 to 80% by weight of gum base. In one embodiment the chewing gum composition comprises from 60 to 65% by weight of gum base. In one embodiment the chewing gum composition comprises more than 40% by weight of gum base. In one embodiment the chewing gum composition comprises more than 50% by weight of gum base. In one embodiment the chewing gum composition comprises more than 55% by weight of gum base. In one embodiment the chewing gum composition comprises more than 60% by weight of gum base, such as more than 70% by weight of gum base, such as more than 75% by weight of gum base, or such as more than 79% by weight of gum base. It is surprising that a chewing gum composition according to the invention with a higher amount of gum base compared to chewing gums known in the art actually increase saliva flow in this group of patients as a skilled person possibly would expect otherwise. Normally it is well known that sweetener, flavour and acid stimulate the saliva flow but in this formulation these stimulants has been left out and surprisingly the high load of soft gum base are able to stimulate alone.

In the examples 1 to 8 and the clinical trial experimental, two different gum bases are presented—a standard gum base and a bubble gum gum base. The standard gum base is more robust and able to give a stable form product and the bubble gum gum base has a more soft and easy chew. A combination of the two different gum base compositions are in one embodiment preferably used to gain the best chewy sensation and to ensure a form stable end product.

In the examples 9 to 13 a third gum base is presented. In one embodiment this third gum base, GB-3, is used to gain the best chewy sensation and to ensure a form stable end product.

The chewing gum composition according to the present invention comprises substantially no flavour ingredients meaning that the chewing gum composition is substantially free of flavour ingredients. It is surprising that the chewing gum composition according to the invention actually increase saliva flow as a skilled person would expect a less pronounced effect due to the common knowledge that flavours in a chewing gum composition increase saliva flow. However the absence of flavours in the chewing gum composition, actually increased saliva flow in head and neck cancer patients which is surprising. Head and neck cancer patients often experience that during and after radiotherapy treatment the oral cavity is highly sensitive due to decreased salivary flow rate, thicker saliva, and alterations to the sense of taste so perhaps the lack of flavours altered the undertaste for the patients thereby actually increasing the saliva flow. The present study surprisingly revealed that it is very important to make the product as taste neutral as possible possibly due to the fact that, for this patient group, a lot of intake taste like metal. So the chewing gum composition according to the present invention has a neutral taste. By the word "substantially" in "substantially no flavour ingredients" is meant that the chewing gum composition comprises from 0.0 to 1.5% by weight of flavour ingredients, such as less than 1% by weight of flavour ingredients, such as less than 0.5% by weight of flavour ingredients such as less than 0.2% by weight of flavour ingredients, such as less than 0.1% by weight of flavour ingredients or such as 0% by weight of flavour ingredients.

In an embodiment of the invention the chewing gum composition can comprise very small amount of flavour where the flavour does not have or only have a very small impact on the taste of the chewing gum composition. A very small amount of flavour can in one embodiment be incorporated into the chewing gum composition to mask the presence of an unwanted taste coming from other ingredients.

Non-exhaustive examples of flavours suitable in embodiments of the present invention are coconut, coffee, chocolate, vanilla, grape fruit, orange, lime, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, eucalyptus, and mint, fruit essence such as from apple, pear, peach, strawberry, apricot, raspberry, cherry, pineapple, and plum essence. The essential oils include peppermint, spearmint, menthol, eucalyptus, clove oil, bay oil, anise, thyme, cedar leaf oil, nutmeg, and oils of the fruits mentioned above.

In addition to the high amount of gum base in the chewing gum composition, the chewing gum composition also comprise a bulk portion comprising chewing gum ingredients that may be mixed into the gum base matrix after it has been made.

One ingredient of this bulk portion is sugar alcohols. By the phrase "sugar alcohols" is meant substances also known as polyols, for example erythritol, lactitol, manitol and isomalt.

In one embodiment of the invention the chewing gum composition comprises at least one polyol in the amount of from 5 to 25% by weight of the chewing gum composition, such as from 10 to 15% by weight of the chewing gum composition. In another embodiment of the invention the chewing gum composition comprises at least one polyol in the amount of from 20 to 75% by weight of the chewing gum composition, such as from 20 to 30% by weight of the chewing gum composition. In one embodiment at least one of the polyols is mannitol.

One ingredient of this bulk portion is softeners. In one embodiment of the invention the chewing gum composition comprises at least one softener. In one embodiment the at least one softener are present in the amount of from 0 to 15% weight of the chewing gum composition, such as from 0 to 8% weight of the chewing gum composition, such as from 0 to 4% weight of the chewing gum composition. In one embodiment the at least one softener are present in the amount of from 1 to 15% weight of the chewing gum composition. In one embodiment the at least one softener are present in the amount of from 2 to 8% weight of the chewing gum composition. In one embodiment the said chewing gum composition comprises two softeners. The softeners are in one embodiment lecithin and triacetine. The lecithin softener is in one embodiment present in the amount of from 2 to 4% weight of the chewing gum composition. The triacetine softener is in one embodiment present in the amount of from 2 to 4% weight of the chewing gum composition. The softeners that are added to the bulk portion of the chewing gum are there to add some more elasticity improving the chew-fell experienced by the user. This patient class has restrained chew muscles so it is important that the chewing gum composition is soft and elastic so that the chewing process becomes easy.

In one embodiment of the invention, the chewing gum composition comprises glycerol. The glycerol is in one embodiment present in the amount of from 0 to 10% weight of the chewing gum composition, such as from 1 to 4% weight of the chewing gum composition. The glycerol is in one embodiment present in the amount of from 2 to 4% weight of the chewing gum composition. The glycerol is working as a humectant in the chewing gum composition.

One ingredient of this bulk portion is fat. In one embodiment of the invention the chewing gum composition comprises a low melting vegetable hydrogenated fat with melting point between 35-45° C. In one embodiment the fat is present in the amount of from 0 to 30% by weight of the chewing gum composition, such as from 1.5 to 30% by weight of the chewing gum composition, such as from 1.5 to 20% by weight of the chewing gum composition, such as in the range of 2 to 10% by weight, such as from 5 to 10% by weight of the chewing gum composition, such as from 8 to 9% by weight of the chewing gum composition or such as in the range of 2 to 5% by weight, such as in the range of 2 to 3% by weight of the chewing gum composition. In one embodiment the fat is present in the amount of 8.5% by weight of the chewing gum composition. In one preferred embodiment the fat used in the describe formulation is a coconut fat but any fat having a low melting point can be used, different kind of vegetable oils could also be used. The preferred oils include plant oils such as hydrogenated soybean oil, hydrogenated cottonseed oil, hydrogenated vegetable oil, and combinations thereof. Other low melting fats and oils include, but are not limited to, tallow, hydrogenated tallow, and cocoa butter.

In one embodiment the chewing gum composition comprises an antifungal agent. The antifungal agent can be selected from chlorhexidine, miconazol, mycostatin, fluconasole or clotrimazole.

In one embodiment the chewing gum composition comprises a fluoride compound. Fluoride has a neutral taste and will therefore not impact the taste of the chewing gum composition but will aid with the oral care of the patients.

In one embodiment the chewing gum composition comprises an acidulant in the amount of less than 0.5% by weight of the chewing gum composition. It is important that the amount of acidulant is so low that it does not have an impact on the taste, but since acids stimulate the secretion of saliva small amount of acids could be beneficial for the patients.

In an embodiment of the invention the acidulant is an organic acid selected from the group consisting of citric acid, malic acid, tartaric acid, adipic acid, ascorbic acid and other acids found in fruits and vegetables.

Tablet film coating is generally one of two types. One is aqueous film coating where normally water is used as a solvent. Another is non-aqueous film coating where an organic solvent are used. An aqueous solvent is normally preferred since some problems are associated with the non-aqueous film coating like employee safety.

A film coating is a thin polymer-based coat applied to a solid dosage form such as a tablet. The thickness of such a coating is usually between 20-100 µm. Under close inspection the film structure can be seen to be relatively non-homogenous and quite distinct in appearance, from a film forming, from casting a polymer solution on a flat surface. High quality aqueous film coating must be smooth, uniform and adhere satisfactorily to the tablet surface and ensure chemical stability of a drug. Today a side-vented, perforated pan-coater is the most commonly used coating device of tablets. Its air flow system through a perforated pan ensures rapid and continuous drying conditions. The low evaporation capacity of water requires high drying efficiency of aqueous film-coating equipment. Beside of masking of bitter taste the main reason for film coating is that the coated tablets are packed on high-speed packaging machine. And the coating reduces friction and increases packaging rate.

So according to an embodiment of the invention a film coating is applied to the chewing gum composition. In one embodiment the film coating is an aqueous film coating. The film coating has a dry thickness from about 15 to 110 micrometer in one embodiment. The film coating can comprise natural polymers and/or synthetic polymers.

Natural polymers include Shellac, Zein, Cellulose, Starch, High amylose starch, Gelatine, Vegetable gum, Saccharide compounds, Dextrin's, Polydextrose, Pullulan, Tragacanth gum, Guar gum, Acacia gum, Arabic gum, Amylose, High amylase starch, Pectin, Chitin, Gluten, Soy protein isolate, Whey protein isolate, Casein, Hydrogenated vegetable oils, Hydrogenated castor oils, Gum rosins and Wood rosins.

Synthetic polymers include cellulose derivatives such as cellulose ethers including Methyl cellulose (MC), Hydroxyethyl cellulose (HEC), Hydroxypropyl cellulose (HPC), Hydroxyethyl methylcellulose, Hydroxypropyl methylcellulose phthalate (HPMCP), Cellulose acetate and hydroxypropyl methylcellulose (HPMC). Other useful synthetic film-coating agents are acrylic polymers and copolymers, e.g. Polymethacrylates, Methylacrylate ester copolymers, Methacrylic acid copolymers or mixtures of cellulose derivatives and acrylic polymers.

Further useful film coating polymers include Sodium alginate, Ammonium alginate, Hydroxypropylated high amylase starch, Chitosan, Copovidone, Dimethylphthalate, Ethyl lactate, Hypromellose acetate succinate, Maltodextrin, Polyethylene glycol (PEG), Polyethylene oxide, Poly(methylvinyl ether/maleic anhydride), Carboxymethylcellulose sodium, Glyceryl behenate, Glyceryl Palmitostearate, Poloxamer, Polyvinyl alcohol, Povidone (Polyvinylpyrrolidone, PVP), Polyvinyl chloride and Polyurethane. It will be appreciated that the film coating according to the present invention may comprise any combination of the above film-coating polymers.

The choice of film-forming polymer(s) for the film coating of the chewing gum tablet is made with due consideration for achieving the best results in regards to maintaining the softness of the chewing gum and creating possible barrier properties in respect of dissolution and diffusion across the film of moisture. The film coating should maintain the soft texture of the chewing gum composition since these patients often have chewing muscles that are restrained because of radiation sequela. The chewing gum should be easy to chew from the start.

According to one embodiment of the invention, the chewing gum does not comprise any coating, such as sugar coating nor film coating.

According to embodiments of the invention, the chewing gum composition is extruded or cast into any desirable shape creating a piece of gum such as a compressed chewing gum tablet or an extruded chewing gum. The chewing gum composition has in one embodiment the weight of from 0.4 to 1.2 gram per piece of gum, such as from 0.45 to 0.8 gram per piece of gum, such as from 0.5 to 0.7 gram per piece of gum. The chewing gum composition has in one embodiment the weight of from 0.5 to 1.5 gram per piece of gum, such as from 0.7 to 1.2 gram per piece of gum, such as from 0.9 to 1.1 gram per piece of gum or around 1 gram per piece of gum.

The test group of the study presented herein in examples 1 to 8 and the clinical trial experimental preferred gum pieces having a size around 0.5 gram/piece as this small size made it easy to chew regardless of rigid muscles or oral sensitivity. The chewing gum disclosed in the clinical trial experimental has a high amount of gum base. When a lower amount of gum base is present in the chewing gum, the chewing gum can have a larger size due to the lower amount of gum base as is the case in the examples 9 to 13, where the gum pieces is having a size around 1.0 gram/piece but also easy to chew regardless of rigid muscles or oral sensitivity.

In the manufacturing of the chewing gum, a conventional mechanical mixing procedure is preferably used. The gum base is added to a running mixer and mixed before the rest of the ingredients of the chewing gum composition are added to the mixer. Obviously, the amount of ingredients used may be varied within the scope of the present invention. The entire mixing procedure typically takes from five to fifteen minutes, but longer mixing times may sometimes be required. Those skilled in the art will recognize that many variations of the above-described procedure may be followed, including the one-step method described in US patent application 2004/0115305 hereby incorporated by reference. Chewing gum is formed by extrusion, compression, and/or rolling and may be centre filled with liquids and/or solids in any form. When manufacturing a compressed chewing gum tablet another method is applied, which is basically very different from the above described, but may broadly be described as an initial conventional mixing of the gum base, as above described, followed by a granulation of the obtained gum base mix. The obtained chewing gum granules may then be mixed with further chewing gum ingredients. This final granule mix may then be compressed into a chewing gum tablet under high pressure and typically with cooling applied. For each compression a layer is made and in this way it is possible to make multi-layered chewing gum, such as two, three or four layers, wherein each layer may include an individual composition.

If a low-calorie gum is desired, a low-caloric bulking agent can be used. Examples of low caloric bulking agents include polydextrose, Raftilose, Raftilin, fructooligosaccharides (NutraFlora(R)), palatinose oligosaccharides; guar gum hydrolysates (e.g. Sun Fiber(R)) or indigestible dextrins (e.g. Fibersol(R)). However, other low-calorie bulking agents can be used.

In some embodiments, one or more colours can be included. As classified by the United States Food, Drug, and Cosmetic Act (21 C.F.R. 73), colours can include exempt from certification colours (sometimes referred to as natural even though they can be synthetically manufactured) and certified colours (sometimes referred to as artificial), or combinations thereof. In some embodiments, exempt from certification or natural colours can include, but are not limited to annatto extract, (E 160b), bixin, norbixin, astaxanthin, dehydrated beets (beet powder), beetroot red/betanin (E 162), ultramarine blue, canthaxanthin (E161g), cryptoxanthin (E161c), rubixanthin (E161d), violanxanthin (E161e), rhodoxanthin (El 610, caramel (E150(a-d)), beta-apo-8'-carotenal (E160e), beta-carotene (E160a), alpha carotene, gamma carotene, ethyl ester of beta-apo-8'-carotenal (E1600f), fiavoxanthin (E161a), lutein (E161b), cochineal extract (E120); carmine (E132), carmoisine/azorubine (E122), sodium copper chlorophyllin (E141), chlorophyll (E140), toasted partially defatted cooked cottonseed flour, ferrous gluconate, ferrous lactate, grape color extract, grape skin extract (enocianina), anthocyanins (E163), haematococcus algae meal, synthetic iron oxide, iron oxides and hydroxides (E172), fruit juice, vegetable juice, dried algae meal, tagetes (Aztec marigold) meal and extract, carrot oil, corn endosperm oil, paprika, paprika oleoresin, phaffia yeast, riboflavin (E101), saffron, titanium dioxide, turmeric (E100), turmeric oleoresin, amaranth (E123), capsanthin/capsorbin (E160c), lycopene (E160d), and combinations thereof.

In some embodiments, certified colours can include, but are not limited to, FD&C blue #1, FD&C blue #2, FD&C green #3, FD&C red #3, FD&C red #40, FD&C yellow #5 and FD&C yellow #6, tartrazine (E102), quinoline yellow (E104), sunset yellow (E110), ponceau (E124), erythrosine (E127), patent blue V (E131), titanium dioxide (E171), aluminum (E173), silver (E174), gold (E175), pigment rubine/lithol rubine BK (E180), calcium carbonate (E170), carbon black (E153), black PN/brilliant black BN (E151), green S/acid brilliant green BS (E142), and combinations thereof. In some embodiments, certified colours can include FD&C aluminum lakes. These consist of the aluminum salts of FD&C dyes extended on an insoluble substrate of alumina hydrate. Additionally, in some embodiments, certified colours can be included as calcium salts.

The present invention also provide a dosage regimen for administering the chewing gum composition for alleviation of xerostomia induced by radiotherapy treatment. So in one embodiment of the invention the chewing gum composition is administered to a human subject before and/or during and/or after radiotherapy treatment. In one embodiment the chewing gum composition is administered to a human subject directly after start up of the radiotherapy treatment. In one embodiment the chewing gum composition is administered to a human subject during the time period of radiotherapy treatment. In one embodiment the chewing gum composition is administered to a human subject in the time period following the radiotherapy treatment. In one embodiment the chewing gum composition is administered to a human subject up to 1 year after end of the radiotherapy treatment. Xerostomia can become a problem already at the beginning of the radiotherapy treatment and maintain a problem long after treatment has ended therefore it can be beneficial to start using the chewing gum composition according to the present invention already at the start of the treatment with radiotherapy.

In one embodiment of the invention the dosage regimen comprises administering the chewing gum composition according to the present invention to a human subject within 20 minutes, such as 15 minutes, such as 10 minutes or such as 5 minutes before each meal. Radiotherapy may result in eating difficulties and unintended weight loss, but by using the chewing gum composition according to the present invention right before the meal, the discomfort experienced by the patients can be alleviated. Since the chewing gum composition according to the present invention may increase saliva output and may decrease the density of the saliva, it is surprisingly beneficial to administer the composition before a meal. First of all, this will stimulate the saliva flow which will easy the eating and secondly, it will also stimulate the chewing muscles so that they are ready to chew the meal to come. So the present invention can also be used for treating or alleviating lack of appetite which often is a side effect after radiotherapy treatment.

In one embodiment of the invention the chewing gum composition according to the present invention is administered to a human subject during times with increased respiration rate, e.g. during physical exercise. During physical exercise the mouth has a tendency to dry out. As this patient group already has a dry mouth it can be a reason not to exercise. By chewing the gum composition according to the present invention alleviation of the dry mouth during exercise can result.

In one embodiment of the invention the chewing gum composition according to the present invention is administered to a human subject up to 10 times per day, such as up to 8 times per day. The patients should use the gum whenever needed to alleviate their xerostomia. In one embodiment the chewing gum composition is administered every 3 to 4 hours up to 10 times per day.

Another scope of the present invention is to provide a chewing gum composition comprising a high amount (such as more than 60% by weight) of gum base and substantially no flavour ingredients. The chewing gum composition can be defined according to the embodiments listed above in relation to the chewing gum composition for use in the alleviation of xerostomia induced by radiotherapy treatment where the chewing gum composition comprises gum base and substantially no flavour ingredients. In one embodiment the chewing gum composition is used as a medical device for use in the alleviation of xerostomia induced by radiotherapy treatment.

Another scope of the present invention is to provide a non-medical use of a chewing gum composition comprising a gum base (e.g. in more than 60% by weight) and substantially no flavour ingredients for use in the alleviation of xerostomia induced by radiotherapy treatment. Hereby is obtained that salivary secretion is increased for patients suffering from radiation induced xerostomia. The salivary secretion is increased up to 20% or up to 30%. In addition, by using the chewing gum composition according to the present invention the composition of the saliva becomes less thick. By means of the chewing gum according to the present invention, applicant showed with the presented study that the chewing gum was able to stimulate and increase the mean salivary output for twenty consecutive participants. This study confirmed that tasteless (86% of the test subjects liked the taste), soft (71% of the test subjects liked the texture), juicy (88% of the test subjects like the juiciness) chewing gum was able to stimulate the remaining function of residual salivary glands into increasing the saliva flow, and contributed to a positive altering in xerostomia and improved oral well-being reported by the patients. The non-medical use can be defined according to the embodiments listed above in relation to the chewing gum composition for use in the alleviation of xerostomia induced by radiotherapy treatment where the chewing gum composition comprises gum base and substantially no flavour ingredients.

Another scope of the present invention is to provide a method of alleviation of xerostomia induced by radiotherapy treatment by the use of a chewing gum composition comprising a gum base (e.g. in more than 60% by weight) and substantially no flavour ingredients. The method can be defined according to the embodiments listed above in relation to the chewing gum composition for use in the alleviation of xerostomia induced by radiotherapy treatment where the chewing gum composition comprises gum base and substantially no flavour ingredients.

When describing the embodiments of the invention, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments.

It should be noted that the above-mentioned means of implementation illustrate rather than limit the invention, and that those skilled in the art will be able to suggest many alternative means of implementation without departing from the scope of the appended claims. Rather, the words used in the specification are words of description rather than limitation, and it is understood that various changes may be made without departing from the scope of the invention. The word 'comprising' does not exclude the presence of other elements or steps than those listed in a claim.

Experimental:

The following non-limiting examples illustrate different variations of the present invention. The examples are meant for indicating the inventive concept; hence the mentioned examples should not be understood as exhaustive for the present invention.

The purpose of the below study was to investigate the use of a chewing gum according to the invention as a salivary stimulant in head and neck cancer patients treated with radiotherapy. We hypothesised that by using chewing gum on a regular daily basis, the saliva flow would be stimulated from the residual functional salivary gland, and thereby improving the oral wellbeing of the patient and increase nutrition intake.

EXAMPLE 1

Preparation of Gum Base 1—also Referred to as Gum Base Standard.

The composition of a gum base 1 is presented in Table 1.

TABLE 1

Gum base 1 composition. Amounts are given in wt-% of the gum base.

|  | GB std. |
|---|---|
| Elastomer | 16.0 |
| Resins | 44.5 |
| Filler | 15.0 |
| Plasticizers | 24.4 |
| Antioxidant | 0.1 |

GB = Gum Base.

The preparation of gum base is carried out by first adding a high-molecular weight elastomer, synthetic resin and filler to a heated (about 120° C.) and running z-blade mixer. After about twenty minutes of mixing, natural resin is added to the running mixer and mixing is continued for about five minutes followed by addition of further natural resin. After about five minutes of continued mixing, some plasticizer and further elastomer are added to the running mixer, and mixing is continued for about five minutes before addition of further plasticizer and antioxidant to the running mixer. Mixing is continued for about half an hour to one hour, and the final gum base mass is emptied from the mixer into coated or lined pans, extruded or cast into any desirable shape. Those skilled in the art will recognize that many variations of the above-described procedure may be followed.

EXAMPLE 2

Preparation of Gum Base 2 also Referred to as Gum Base Bubble.

The composition of a gum base 2 is presented in Table 2.

TABLE 2

Gum base 2 composition. Amounts are given in wt-% of the gum base.

|  | GB-Bubble |
|---|---|
| Elastomer | 11.9 |
| Resins | 44.0 |
| Filler | 19.0 |
| Plasticizers | 25.0 |
| Antioxidant | 0.1 |

GB = Gum Base.

There is a different between the two gum bases GB-std. and GB-Bubble, where the GB-std. is more robust and able to give a stable form product and the GB-Bubble has a more soft and easy chew. A combination of two different gum bases is often used to be able to obtain the best chewy sensation for the different formulations and to ensure form stable products.

The Gum base 2 (GB-Bubble) has a higher level of synthetic resins with high molecular weight to give a stronger film with improved ability to preform bubbles compare to Gum base 1.

Preliminary Experimental:

EXAMPLE 3

Preparation of Standard Chewing Gum

In the present example, a standard chewing gum has been listed. Gum base 1 from example 1 "GB std." in combination with the gum base 2 "GB bubble" from example 2 was made into chewing gum CG with the composition as described in Table 3.

TABLE 3

Chewing gum composition for a standard chewing gum. Amounts are given in % by weight of the chewing gum formulation. CG = Chewing Gum

|  | CG std. |
|---|---|
| GB 1-std. | 20.0 |
| GB 2-bubble | 20.0 |
| Bulk sweetener Sorbitol | 51.6 |
| Bulk sweetener/softener Maltitol syrup | 4.0 |
| Softener: Lecitin | 0.2 |
| Flavour | 3.5 |
| High intensive sweetener | 0.75 |

A conventional mechanical mixing procedure is used. The gum base is added to a mixing kettle provided with mixing means like e.g. horizontally placed Z-shaped arms. The kettle had been preheated to a temperature of up to approximately 50° C., and the other ingredients are added according to a time schedule. Obviously, the amount of ingredients used may be varied within the scope of the present invention.

EXAMPLE 4

Preparation of a Tasteless Chewing Gum Composition

Head and neck cancer patients treated with radiotherapy has the following issues: low saliva flow, thick saliva, nausea—the paitient can't tolerate larger pieces of gum in the mouth, everything taste of metal, no tolerance of sweet taste is accepted since it leads to nausea. Therefore are the following criteria important when formulating a chewing gum for this patient group: The chewing gum should be tasteless, without flavour, wetness or acid, it should be rather small, and it should be soft and should not dry out the oral cavity.

By trying different sizes of chewing gum; 2 gram, 1.5 gram, 1 gram, 0.5 gram and 0.3 gram, on a few head and neck cancer patients a size of approx. 0.5 gram was selected.

The pure gum base pieces (pellets) from example 1 and example 2 have been tested in regards to taste, texture and size. The results of the evaluation showed that the texture was found to be too hard and not elastic enough, the size too small (0.3 gram) and the taste neutral. The neutral taste was acceptable—but the mouth feel was to dry.

In the present examples, standard chewing gum formulations without added flavour are listed in Table 4.

TABLE 4

Chewing gum composition for tasteless chewing gum. Amounts are given in % by weight of the chewing gum formulation.

|  | Tasteless CG-1 | Tasteless CG-2 | Tasteless CG-3 |
| --- | --- | --- | --- |
| GB 1 - std. | 20.0 | 20.0 | 20.0 |
| GB 2 - bubble | 20.0 | 20.0 | 20.0 |
| Bulk sweetener Sorbitol | 55.1 | 55.9 | 57.9 |
| Bulk sweetener/softener Maltitol syrup | 4.0 | 4.0 |  |
| Softener: Lecitin | 0.2 | 1 | 2 |
| High intensive sweetener | 0.75 |  |  |

CG = Chewing Gum

The organoleptic evaluation showed that:

| Tasteless CG-1 | Removing the flavour leads to a sweet chewing gum with a hard texture - need more softener. |
| --- | --- |
| Tasteless CG-2 | Removing the flavour and high intensive sweetener and increasing the softener give a softer texture - but still too sweet. |
| Tasteless CG-3 | Removing the flavour, high intensive sweetener, maltitol syrup and increasing the softener - gives a softer texture, but still too sweet. |

EXAMPLE 5

Gum Base Amount

Formulation with different amount of gum base has been tried. When the amount of gum base is reduced the chewing gum residue is evaluated too small—therefore higher gum base percentages will be needed.

TABLE 5

Gum base amount in % by weight of the chewing gum formulation.

| Sample no. | Gum base | | Taste and mouthfeel comment |
| --- | --- | --- | --- |
|  | GB 1 - std. | GB 2 - bubble |  |
| 1 | 20 | 20 | To small chewing gum residue |
| 2 | 30 | 30 | To small chewing gum residue |
| 3 | 30 | 50 | Fine chewing gum residue, could be a bit softer |
| 4 | 13 | 67 | Fine chewing gum residue |

EXAMPLE 6

Preparation of Chewing Gum

In the present example, the gum base 1 from example 1 GB std. in combination with the gum base 2 GB bubble from example 2 was made into chewing gum CG with the composition as described in Table 6. The sorbitol has been replaced with calcium carbonate to avoid the sweetness. To decrease the dryness from calcium carbonate, triacetine has been added in different level.

TABLE 6

Amounts are given in % by weight of the chewing gum formulation.

|  | CG-4 | CG-5 |
| --- | --- | --- |
| GB 1 - std. | 13.0 | 13.0 |
| GB 2 - bubble | 67.0 | 67.0 |
| Filler Calcium carbonate | 17.0 | 15.7 |
| Softener: Lecithin | 2.0 | 2.0 |
| Softener: Triacetine | 1.0 | 2.3 |

CG = Chewing Gum

The taste evaluation of samples from example 6 concluded that the product was too dry due to the calcium carbonate even though the extra softener has been added. The calcium carbonate has been used due to that it has a neutral taste and no sweetness, but the juiciness was missing.

EXAMPLE 7

Preparation of Chewing Gum with Different Polyols

Chewing gums comprising with varying polyols was made to investigate the mouthfeel and taste. The different polyols is replacing the calcium carbonate in formulation CG-5. The setup is listed in Table 7.

TABLE 7

Different polyols tested in chewing gum formulation (calcium carbonate replaced by polyols, formulation CG-5) in regards to taste impact and mouthfeel

| Sample no. | Polyol | | | Taste and mouthfeel comment |
| --- | --- | --- | --- | --- |
|  | Sorbitol | Xylitol | Mannitol |  |
| CG-6 | Added |  |  | Too sweet taste, good mouth feel |
| CG-7 |  | Added |  | Too sweet taste and cooling effect, good mouth feel |
| CG-8 |  |  | Added | Less sweet - close to neutral taste and good mouth feel |

Even with the low contain of polyol added (15.7%) the sorbitol and xylitol had a sweet taste. The mannitol polyol was the one with the most neutral taste profile compared with xylitol and sorbitol. Other polyols as Isomalt and Lactitol is also expected to work.

EXAMPLE 8

Preparation of Chewing Gum with Softer Texture and with more Juiciness

The chewing gums formulation CG-8 in example 7 has been modified with respect to softer texture and increased juiciness. The setup is listed in Table 8.

TABLE 8

Adjustment of softener and fat to achieve a soft juicy chewing gum without flavour. Amounts are given in % by weight of the chewing gum formulation.

|  | CG-8 | CG-9 | CG-10 | CG-11 |
| --- | --- | --- | --- | --- |
| GB 1 - std. | 13.0 | 13.0 | 13.0 | 13.0 |
| GB 2 - bubble | 67.0 | 67.0 | 67.0 | 67.0 |
| Bulk sweetener Mannitol | 15.7 | 14.5 | 13.0 | 11.5 |

TABLE 8-continued

Adjustment of softener and fat to achieve a soft
juicy chewing gum without flavour. Amounts are given
in % by weight of the chewing gum formulation.

|  | CG-8 | CG-9 | CG-10 | CG-11 |
|---|---|---|---|---|
| Softener: Lecithin | 2.0 | 2.5 | 2.5 | 2.5 |
| Softener: Triacetine | 2.3 | 3.0 | 3.0 | 3.0 |
| Fat |  |  | 1.5 | 3.0 |

CG = Chewing Gum

Formulation CG-9 has been optimized with the two softening system to obtain a chewing gum that is soft from the first bit. Normally a standard gum has to be chewed in action before the optimal texture is obtained. Furthermore it would be of high value to be able to remove some of the dryness in the oral cavity. Therefore a fat that is melting in the oral cavity has been added. The idea is to leave a thin fat layer on the surface in the oral cavity lubricant effect, so thin that it gives a pleasant feeling not related to dryness.

Formulation CG-11 with 3% fat added has a good mouth-feel and is therefore the selected formulation for the clinical trials experimental. Formulation CG-11 is a chewing gum that gives a fantastic juiciness, softness from the beginning and leaves the oral cavity with a moist feeling.

The chewing gum formulation may optionally be coated by means of film coating. The coating may e.g. be applied according to conventional film coating methods. The pieces evaluated are without coating.

Clinical Trials Experimental:

Patients

This non-randomised pilot-study was conducted at the Department of Oncology at Odense University Hospital, from 2th Oct. to 20th Dec. 2014. Sixty-two consecutive head and neck cancer patients were invited to participate in the study during their follow-up visits. Patients were eligible for participation when they met the following inclusion criteria: treatment with curative (chemo-) radiotherapy (primary or post-operative); the field of irradiation encompassing all or parts of the major salivary glands; and subject to xerostomia score 1 to 3 rated by the treating physician according to the scoring system from DAHANCA (Jensen K, Jensen A B, Grau C. A cross sectional quality of life study of 116 recurrence free head and neck cancer patients. The first use of EORTC H&N35 in Danish. Acta Oncol. 2006;45:28-37). Enrolment for the study was possible two to twelve months after finishing radiation treatment. No side-effects were reported by the patients completing the study.

Study Design

The aim of the study was to measure whole saliva output before and after using a saliva stimulant. The duration of the study was two weeks, and was completed after two visits to the Department of Oncology. The first visit took place after the patient had finished the planned check-up. No information had been sent to the patient beforehand. At the first visit, information was presented orally and written before the patient decided whether or not to participate. The visit consisted of three constituent elements; first an unstimulated saliva sample; second a questionnaire; and third a stimulated saliva sample. The unstimulated saliva sample was provided by spitting into a test tube for 5 minutes. After a short break, an EORTC H&N35-inspired questionnaire was completed. Then a saliva stimulant in the form of a chewing gum was chewed for 5 minutes supported by a metronome. After depositing the chewing gum, the stimulated saliva sample was obtained by spitting into a second test tube for 5 minutes. A date was found for the second visit two weeks later. During those two weeks, the patient was given chewing gum for use at home. At the second visit, the patient provided an unstimulated saliva sample, completed the same questionnaire, and finished with the stimulated saliva sample.

Chewing Gum

Patients agreeing to participation were provided with chewing gum (samples CG-11) to stimulate whole saliva flow. The chewing gum contained neither taste nor sugar, or had any coating. It was 12×9 mm long and weighted 0.5 g. The patient was instructed to: use the chewing gum during daily activities; three to five times a day; and before regular meals (breakfast, lunch, and dinner).

Saliva Measurement

Saliva samples were measured with regard to weight (g) and volume (mL), and the flow rate (ml/min and g/min) was calculated. For all sample tubes pre- and post-weight were carefully measured on a Mettler Toledo weight (PG4002-S DeltaRange®) with readable intervals to 0.01 g. To determine the exact weight of saliva flow, the weight was calibrated with 500 g, 100 g, and 1 g weights before use. After weighing, all samples were centrifuged at 2000 G at 20 C for 5 minutes before the volume was determined by use of 3 mL pipettes. For this study, the weight of the saliva output was considered most accurate.

Questionnaire

The EORTC H&N35-inspired questionnaire (Jensen K, Jensen A B, Grau C. A cross sectional quality of life study of 116 recurrence free head and neck cancer patients. The first use of EORTC H&N35 in Danish. Acta Oncol. 2006; 45:28-37) consisted of 27 questions regarding xerostomia and the use of chewing gum. Each patient completed the same questionnaire two times; during the first and the second visit. The questionnaire used in the study is found in Appendix I.

Ethics

Written informed consent was obtained from all patients agreeing to participate. This study had been approved by the Regional Scientific Ethical Committees for Southern Denmark.

Statistics

Saliva output was found to be normal distributed. The correlations between measurements of the saliva output were tested using a paired T-test. Patient and tumour characteristics for all eligible patients and responses to the questionnaires were tested by Spearman's correlation for categorical values. All data were analysed according to the principle of intention-to-treat (ITT). A two-sided p-value <0.05 was regarded as significant. Data were analysed using SPSS version 22 for Windows.

Results

Out of sixty-two consecutive patients, thirty-one (50%) agreed to participate in the study. Nine patients were lost to follow-up and two were excluded from the statistical analysis due to screening failure. Twenty consecutive patients completed the study.

Characteristics for all eligible patients are summarised in Table 9 below. The patients declining participation included two screening failures, which should have been excluded from the study due to restricted radiation field (parotid cancer) and inclusion more than twelve months after radiation (18 months follow-up). Non-participants differed from the participating patients by having a tendency to smoke after radiotherapy (27% versus 3% respectively, p=0.01). There was no difference in gender, age, follow-up time after radiation, site, clinical stage or distance to hospital. Fiftyfive percent of the non-participants had finished treatment within 2-5 months. The patients completing the study (n=20) only differed from the patients lost to follow-up regarding chemotherapy. A trend could be seen towards patients lost to follow-up not completing the study after treatment with chemotherapy (p=0.05).

Medical records were reviewed for all consenting patients. Eleven patients were prescribed medication frequently associated with xerostomia including opioids, anticholinergic, antidepressants, antiepileptic, antipsychotics, and smoking cessation medication. Four patients were prescribed more than one drug associated with xerostomia. Six patients lost to follow-up were prescribed medication as mentioned above.

mean saliva output was 0.62 g and 0.82 g (the line at the bottom). The increased saliva output was significant for both visits when tested by the two-sided t-test (p=0.008 and p=0.05, respectively). The increase in mean saliva flow was also significant for both saliva flow rate and volume.

The mean saliva output in relation to the first visit was 0.83 ml for unstimulated and 1.12 ml for stimulated saliva whereas at the second visit, mean saliva output was 0.66 ml and 0.95 ml.

The mean flow rate in relation to the first visit was 0.16 g/min (0.17 ml/min) for unstimulated saliva and 0.21 g/min (0.22 ml/min) for stimulated saliva whereas at the second visit, mean flow rate was 0.13 g/min (0.13 ml/min) and 0.18 g/min (0.19 ml/min).

TABLE 9

Patient and tumour characteristics for all eligible patients from October to December 2014.

|  | Total[a] n = 62 | Non-participants[b] n = 33 | Participants[c] n = 29 | P | Completing the study[d] n = 20 | P[e] |
|---|---|---|---|---|---|---|
| Men | 42 (68%) | 20 (61%) | 22 (76%) | NS | 15 (75%) | NS |
| Age [median] (range, years) | 63 (39-78) | 64 (39-78) | 62 (46-73) | NS | 62 (46-73) | NS |
| Smoking after RT | 10 (16%) | 9 (27%) | 1 (3%) | 0.01 | 0 | NS |
| Follow-up after RT | | | | | | |
| 2-5 months | 34 (55%) | 18 (55%) | 16 (55%) | NS | 10 (50%) | NS |
| 6-9 months | 13 (21%) | 7 (21%) | 6 (21%) | | 5 (25%) | |
| 10-12 months | 14 (23%) | 7 (21%) | 7 (24%) | | 5 (25%) | |
| >12 months | 1 (2%) | 1 (3%) | — | | — | |
| Site | | | | | | |
| Pharynx | 48 (77%) | 25 (76%) | 23 (79%) | NS | 15 (75%) | NS |
| Cavum oris | 10 (16%) | 6 (18%) | 4 (14%) | | 3 (15%) | |
| Saliva gland | 1 (2%) | 1 (3%) | — | | — | |
| Unknown primary tumor | 3 (5%) | 1 (3%) | 2 (7%) | | 2 (10%) | |
| Clinical stage III-IV | 51 (82%) | 27 (82%) | 24 (83) | NS | 16 (80%) | NS |
| Concomitant chemotherapy | 32 (52%) | 14 (42%) | 18 (62%) | NS | 10 (50%) | 0.05 |
| Distance to hospital | | | | | | |
| >50 km[f] | 24 (39%) | 12 (36%) | 12 (41%) | NS | 10 (50%) | NS |
| <50 km[g] | 38 (61%) | 21 (64%) | 17 (59%) | | 10 (50%) | |

Figure 2:
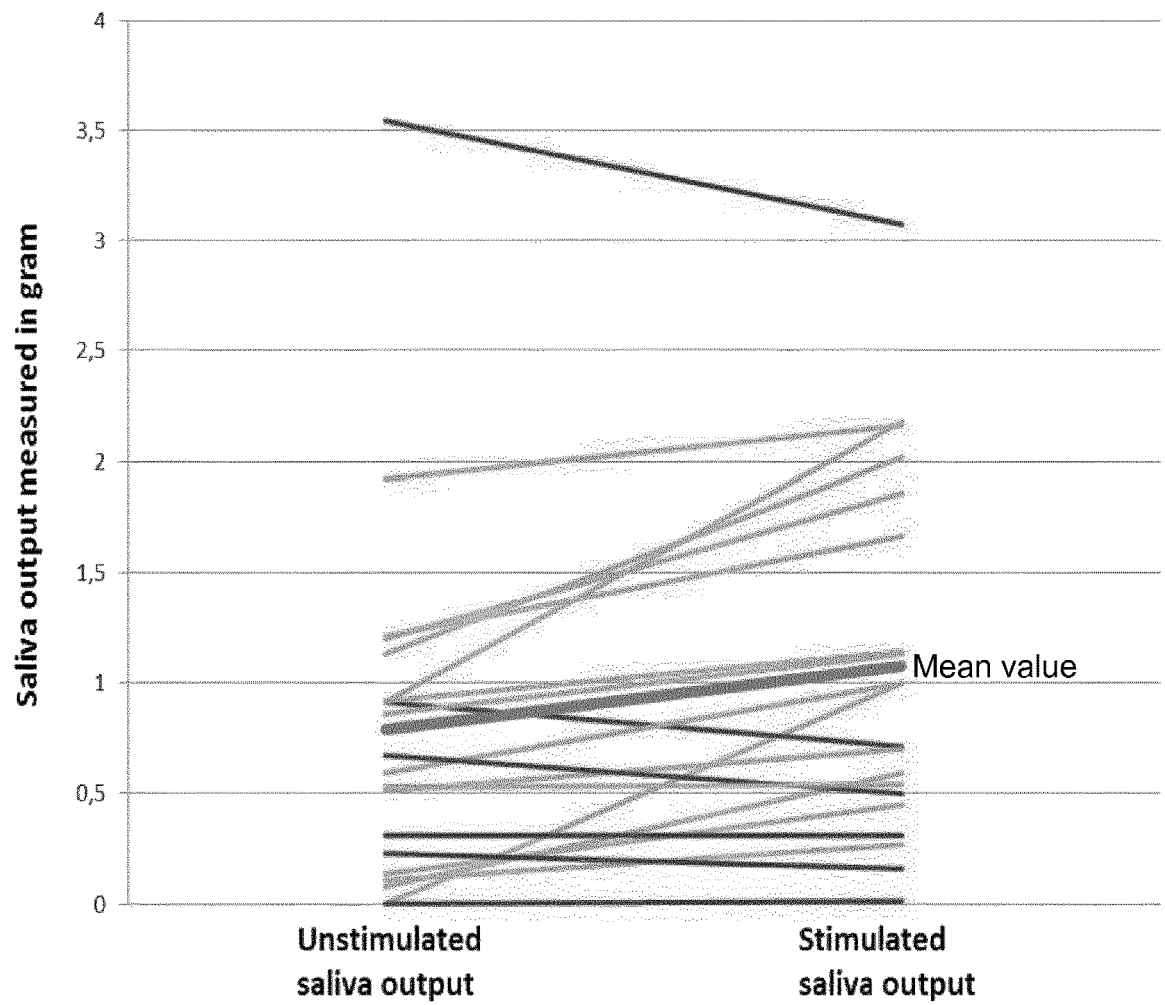
FIG. 2 shows the increase and decrease in saliva output after stimulation with the chewing gum (n=20).

[a]Total number of consecutive and eligible patients asked to participated in the study
[b]Number of patients declining to participate
[c]Number of patients consenting to participate including patients lost to follow up
[d]Number of patients with repeating measurements who complete the study
[e]P-value comparing the patients completing the study with the patients lost to follow up.
[f]Less than 50 km to the hospital (Funen)
[g]More than 100 km to the hospital (Jutland or Zealand)
RT (radiation therapy)
NS is no significant p-value The effect of the chewing gum to modify xerostomia was evaluated by saliva output and the EORTC H&N35-inspired questionnaires. The saliva output was measured in weight (g), volume (mL), and flow rate (g/min and mL/min) for both unstimulated and stimulated saliva. In FIG. 2, the saliva output from the first visit is plotted for all patients completing the study. Fourteen patients had increased in saliva output after stimulation with the chewing gum. The mean value of increased saliva output was 0.28 g (p=0.008).

Figure 3:
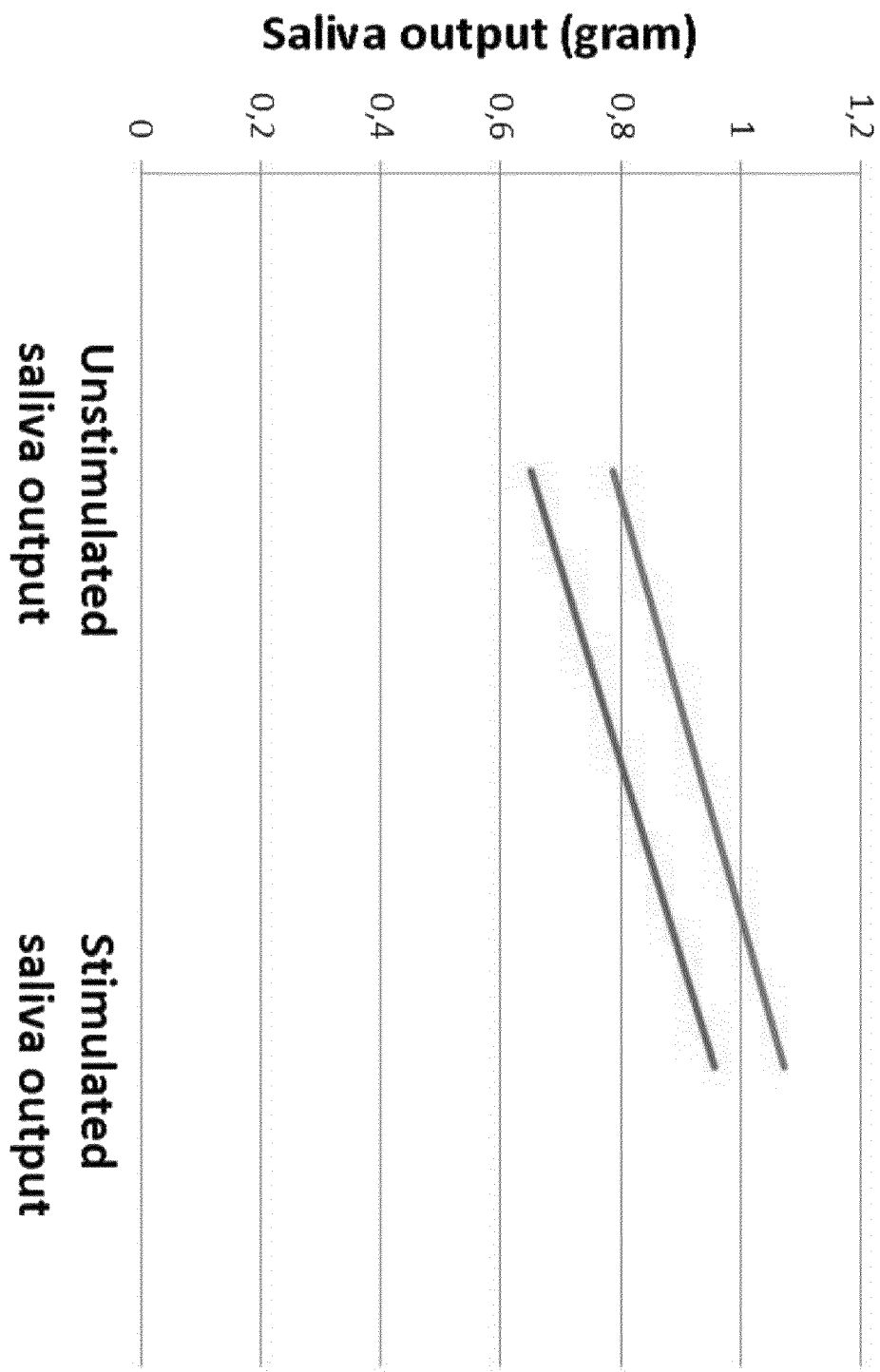
FIG. 3 shows the mean output for unstimulated and stimulated saliva measured in gram. The line at the top shows the mean output after the first visit whereas the line at the bottom shows the mean saliva output after the second visit.

The mean saliva output for all patients with repeating measurement is illustrated in FIG. 3. After the first visit, mean output was 0.79 g for unstimulated and 1.07 g for stimulated saliva (the line at the top). At the second visit, A control group (n=10), consisting of two males (20%), mean age 33 years (range, 25-46), and all non-smokers, were unable to reproduce the results shown in FIGS. 2 and 3 (see table 10 below). Mean saliva output for the control group was 4.01 g for unstimulated and 3.96 g for stimulated saliva. No significant difference was found.

TABLE 10

|  | USTIM | STIM |
|---|---|---|
| Test (n = 29) | 0.84 | 1.04 |
| Kontrol (n = 10) | 4.01 | 3.96 |

Responses to the abbreviated version of the EORTC H&N35-inspired questionnaire from patients with repeated measurements are shown in table 11 below. At the first visit, xerostomia (Q4) was a major compliant, with 90% of the participants rating xerostomia as "quite a bit" or "a lot" (DAHANCA score 2 and 3). At the second visit, only 30% rated xerostomia as "quite a bit". No significant difference was found for the evaluations of xerostomia. Responses showed that fewer patients experienced pain in the mouth or jaw after using the chewing gum for two weeks (p=0.05 and p=0.01). Eighty percent reported an increase in saliva flow (p=0.007), and 75% had less trouble enjoying their meal after the second visit (p=0.004).

Patients reported that they used approximately four pieces of chewing gum per day (Q21, range 0-6); two patients did not use the product daily. The gum was used before two regular meals per day (Q22, range 0-3); three patients did not use the gum before any meals. The same two patients did not make use of the gum on a daily basis or used it before eating. Ninety-five percent of the participants reported that they felt increased saliva flow when using the gum (Q19).

like the juiciness) chewing gum was able to stimulate the remaining function of residual salivary glands into increasing the saliva flow, and contributed to a positive altering in xerostomia and improved oral well-being reported by the patients. For both the first and second visit, saliva flow increased when stimulated by the chewing gum (p=0.008 and p=0.05 respectively). This corresponded well with the patients reporting positive changes to their xerostomia (Q19).

The mean flow rate for unstimulated saliva was 0.13 ml/min after using chewing gum for two weeks. The limit for very low unstimulated whole saliva flow rate was <0.1 ml/min and corresponds with hyposalivation. Looking at all twenty measurements of the unstimulated flow rate (ml/min), eight patients had a very low flow rate below 0.1 ml/min and seven had a low flow rate between 0.1-0.2 ml/min. Comparing the patients' self-rated xerostomia with the measured unstimulated flow rate, eight patients with saliva flow rate <0.1 mL/min rated their xerostomia as severe. Four out of seven patients with flow rate 0.1-0.2 mL/min also rated xerostomia as being severe. This corre-

TABLE 11

Responses to the EORTC H&N35 questionnaire from participants completing the study (n = 20)

| In the past week have you had ... | Visit 1[a] | | | | Visit 2[b] | | | | P[c] |
|---|---|---|---|---|---|---|---|---|---|
| | 1[d] | 2 | 3 | 4 | 1 | 2 | 3 | 4 | |
| Oral cavity | | | | | | | | | |
| Q1 Pain in your mouth? | 13 (65%) | 4 (20%) | 2 (10%) | 1 (5%) | 17 (85%) | 2 (10%) | 1 (5%) | | 0.05 |
| Q2 Pain in you jaw? | 14 (70%) | 4 (20%) | 1 (5%) | 1 (5%) | 18 (90%) | 1 (5%) | 1 (5%) | | 0.01 |
| Q4 A dry mouth? | 1 (5%) | 1 (5%) | 8 (40%) | 10 (50%) | 7 (35%) | 7 (35%) | 6 (30%) | | NS |
| Q5 Sticky saliva? | 4 (20%) | 8 (40%) | 5 (25%) | 3 (15%) | 5 (25%) | 7 (35%) | 7 (35%) | 1 (5%) | NS |
| Q6 Less saliva? | 7 (35%) | 2 (10%) | 5 (25%) | 6 (30%) | 13 (65%) | 3 (15%) | 3 (15%) | 1 (5%) | 0.007 |
| Eating difficulties | | | | | | | | | |
| Q7 Problems swallowing liquids? | 13 (65%) | 6 (30%) | 1 (5%) | | 15 (75%) | 4 (20%) | 1 (5%) | | NS |
| Q8[x] Problems swallowing solid food? | 7 (35%) | 5 (25%) | 4 (20%) | 3 (15%) | 6 (30%) | 8 (40%) | 5 (25%) | 1 (5%) | NS |
| Q11 Decreased sense of taste? | 8 (40%) | 4 (20%) | 3 (15%) | 5 (25%) | 12 (60%) | 4 (20%) | 3 (15%) | 1 (5%) | 0.01 |
| Q13 Trouble enjoying your meals? | 5 (25%) | 3 (15%) | 7 (35%) | 5 (25%) | 6 (30%) | 9 (45%) | 4 (20%) | 1 (5%) | 0.004 |
| Q14 Trouble eating with other people? | 12 (60%) | 4 (20%) | 3 (15%) | 1 (5%) | 10 (50%) | 6 (30%) | 4 (20%) | | NS |

[a]Responses from the first visits when the patient is recruited
[b]Responses from the second visit after using chewing gum for two weeks
[c]The p-value was found by using a paired T-test
[d]Responses to the questionnaire: 1 is "None", 2 is "A little", 3 "Quite a bit", and 4 is "A lot".
Q is the number of the question in the questionnaire.
[x]Q8: one response is missing from questionnaire 1
NS is no significant p-value Conclusion from the Clinical Study The purpose of this study was to increase salivary secretion for patients suffering from radiation induced xerostomia. By means of a chewing gum, the study was able to stimulate and increase the mean salivary output for twenty consecutive participants. This study confirmed that tasteless (86% of the test subjects liked the taste), soft (71% of the test subjects liked the texture), juicy (88% of the test subjects sponds with findings from Wolff et al, saying that symptoms of xerostomia become evident with saliva flow about 0.1-0.2 mL/min (Wolff M, Kleinberg I. Oral mucosal wetness in hypo- and normosalivators. Arch Oral Biol. 1998;43:455-62).

Mean unstimulated saliva output decreased after the second visit compared to unstimulated saliva output at the first visit (FIG. 3). The decline in unstimulated saliva flow at the second visit may be explained by the short period of time allotted for the patient to adapt to the chewing gum, failure to use it on a regular basis, or progressing xerostomia after radiotherapy. The circadian rhythm and fasting may also affect saliva secretion in patients with hyposalivation (Flink H, Tegelberg A, Lagerlof F. Influence of the time of measurement of unstimulated human whole saliva on the diagnosis of hyposalivation. Arch Oral Biol. 2005;50:553-9). In this study, measurement of saliva flow took place throughout the day with no regard to saliva's circadian rhythm. Prescribed medication diminishing saliva flow and may have affected the results. The unstimulated saliva flow for five patients taking opioids was reduced, with one patient having very low saliva flow (<0.1 ml/min) and two having low saliva flow (0.1-0.2 ml/min) at the first visit. A saliva stimulant might have a positive effect on medication induced xerostomia, as the salivary glands are not permanently damaged.

EXAMPLE 9

Preparation of Gum Base 3 also Referred to as GB 3.
The composition of a gum base 3 is presented in Table 12.

TABLE 12

Gum base 3 composition. Amounts are given in wt-% of the gum base.

|  | GB-3 |
|---|---|
| Elastomer | 11.6 |
| Resins | 39.6 |
| Filler | 21.7 |
| Plasticizers | 27.0 |
| Antioxidant | 0.1 |

GB = Gum Base.

The GB 3 is a different from the two other gum bases presented herein; GB std. and GB-bubble; it is more firm and robust due to higher content of higher molecular weight of elastomer.

The preparation of gum base is carried out by first adding a high-molecular weight elastomer, synthetic resin and filler to a heated (about 120° C.) and running z-blade mixer. After about twenty minutes of mixing, natural resin is added to the running mixer and mixing is continued for about five minutes followed by addition of further natural resin. After about five minutes of continued mixing, some plasticizer and further elastomer are added to the running mixer, and mixing is continued for about five minutes before addition of further plasticizer and antioxidant to the running mixer. Mixing is continued for about half an hour to one hour, and the final gum base mass is emptied from the mixer into coated or lined pans, extruded or cast into any desirable shape. Those skilled in the art will recognize that many variations of the above-described procedure may be followed.

EXAMPLE 10

Preparation of a Chewing Gum with a Larger Size.
By increasing the size of the chewing gum, the production will be a bit easier, but by the same time decreasing the amount of gum base; the rest volume (after chewing for a while) will still be in an appropriate size and the patient will still find the size of the piece of gum acceptable.
The different size and gum base level has been listed in Table 13.

TABLE 13

Adjustment of size and gum base level

|  | CG-11 | CG-12 | CG-13 |
|---|---|---|---|
| Size | 0.5 gram | 1 gram | 1 gram |
| GB amount | 80% | 80% | 60% |

When increasing the size, the chewing gum residue also increases (comparison between sample CG-11 and CG-12). When sample CG-12 and CG-13 is compared; sample CG-12 has a higher chewing gum residue than CG-13 and CG-13 rest volume was evaluated acceptable. Furthermore CG-12 was more difficult to manufacturing and more deform than sample CG-13. The selected sample was CG-13 but with the conclusion that it is still being to deform, soft and sticky.

EXAMPLE 11

Preparation of Chewing Gum with Focus on Improving the Manufacturing Process.
To make the formulation les sticky the GB-Bubble was removed from the formulation and a formulation with only GB-3 was preparred. The obtained formulation was moving in the right direction regards to firm stability but still not good enough.
Therefore different amount of softener has been investigated and is listed in Table 14.

TABLE 14

Adjustment of softener levels, amounts are given in wt-%.

|  | CG-14 | CG-15 | CG-16 | CG-17 | CG-17 |
|---|---|---|---|---|---|
| GB-3. | 60.0 | 60.0 | 60.0 | 60.0 | 60.0 |
| Bulk sweetener Mannitol | 31.5 | 34.3 | 35.5 | 35.8 | 37.0 |
| Softener: Lecitin | 2.5 | 1.2 |  | 1.2 |  |
| Softener: Triacetine | 3.0 | 1.5 | 1.5 |  |  |
| Fat | 3.0 | 3.0 | 3.0 | 3.0 | 3.0 |

A conventional mechanical mixing procedure is used. The gum base is added to a mixing kettle provided with mixing means like e.g. horizontally placed Z-shaped arms. The kettle had been preheated to a temperature of up to approximately 50° C., and the other ingredients are added according to a time schedule. Obviously, the amount of ingredients used may be varied within the scope of the present invention.

By varying the amount of the two different softeners, lecitin and triacetine, we found that when they were present in lower amount—a more robust product was obtained. Furthermore lecitin has an off note and by removing both lecitin and triacitine a more robust (sample CG-17) and more taste neutral product was obtained. However, the issues were that the product felt dry and hard.

EXAMPLE 12

Preparation of Chewing Gum with more Juiciness and Softer Chew.
To make a less dry chewing gum higher amount of fat has been tested. The fat has this lubricant effect that reduces the dryness.
Different amount of fat has been tested in Table 15.

TABLE 15

Adjustment of fat level. Amounts are given in wt-%.

|  | CG-18 | CG-19 | CG-20 | CG-21 |
|---|---|---|---|---|
| GB-3. | 60.0 | 60.0 | 60.0 | 60.0 |
| Bulk sweetener Mannitol | 37.0 | 34.0 | 31.5 | 30.0 |
| Softener: Lecitin |  |  |  |  |
| Softener: Triacetine |  |  |  |  |
| Fat | 3.0 | 6.0 | 8.5 | 10.0 |

The lubricant effect was increased when the level of fat was increased. But for sample CG-21 with a fat level at 10% the formulation was sticky during manufacturing and also the surface of the tablets was sticky. The firm stability was also affected by the high amount of fat. The selected formulation is sample CG-20 that has a nice lubricant effect and is more processable.

To obtain an even better juiciness; glycerol has been tested in 2 levels (2% glycerol and 4% glycerol) for the formulation CG-20. The glycerol had a very good effect on the juiciness and also helps to ensure that the chewing gum doesn't so easily dry out during manufacturing. The function of glycerol in the chewing gum is being a humectant. The 2% glycerol was selected due to manufacturing.

EXAMPLE 13

Increasing the dimensions/firm stability and robustness:
The two gum bases GB-std. and GB-3 are compared in Table 16, and the results shows that when GB-3 is used a more robust gum base is obtained.

TABLE 16

Test of 2 different types of gum bases and the effect of hardness.

|  | CG-24 | CG-25 |
|---|---|---|
| GB-std. | 65.0% |  |
| GB-3 |  | 65.0% |
| Bulk sweetener Mannitol | 24.5% | 24.5% |
| Softener: Lecitin |  |  |
| Softener: Triacetine |  |  |
| Fat | 8.5% | 8.5% |
| Glycerol | 2% | 2% |
| Hardness day 1 | 2.3N | 4.6N |
| Hardness day 2 | 2.8N | 6.2N |

Sample CG-25 is as expected more robust the when the GB-std. is used. In this formulation the robustness has been obtain and at the same time a juicy, lubricant and soft texture has been achieved.

TABLE 17

Questionnaire survey

Name:　　　　　CPR:　　　　　Date:　　　　　Time.

In the past week:

|  |  | None | A little | Quite a bit | A lot |
|---|---|---|---|---|---|
| 1. | Have you had pain in your mouth? | 1 | 2 | 3 | 4 |
| 2. | Have you had pain in you jaw? | 1 | 2 | 3 | 4 |
| 3. | Have you had a painful throat? | 1 | 2 | 3 | 4 |
| 4. | Have you had a dry mouth? | 1 | 2 | 3 | 4 |
| 5. | Have you had sticky saliva? | 1 | 2 | 3 | 4 |
| 6. | Have you had less saliva? | 1 | 2 | 3 | 4 |
| 7. | Have you had problems swallowing liquids? | 1 | 2 | 3 | 4 |
| 8. | Do you have enough saliva to chew and swallow your food? | 1 | 2 | 3 | 4 |
| 9. | Have you had problems with your sense of smell? | 1 | 2 | 3 | 4 |
| 10. | Have you had a positive change of your sense of taste? | 1 | 2 | 3 | 4 |
| 11. | Have you had problems with your sense of taste? | 1 | 2 | 3 | 4 |
| 12. | Have you had problems with your teeth? | 1 | 2 | 3 | 4 |
| 13 | Have you had trouble enjoying your meals? | 1 | 2 | 3 | 4 |
| 14. | Have you had trouble eating with other people? | 1 | 2 | 3 | 4 |
| 15. | Have you had soreness in your mouth when using the chewing gum? | 1 | 2 | 3 | 4 |
| 16. | Have you used pain-killers? |  | No | Yes |  |
| 17. | Have you eaten food with a different texture? |  | No | Yes |  |
| 18. | Would you like to use the chewing gum after the ending of this test? |  | No | Yes |  |
| 19. | Have you had increased saliva flow or moist mouth after using the chewing gum? |  | No | Yes |  |
| 20 | If you answered "yes" to Question 19, please describe for how long the effect lasts? |  |  |  |  |
| 21. | How many times per day did you use the chewing gum? | 0　1 | 2　3 | 4　5 | More than 5 per day |
| 22. | How many times per day did you use the chewing gum before a meal? | 0 | 1　2 | 3 | 4 |
| 23. | How many pieces of chewing gum did you use before a meal? | 0 | 1　2 | 3 | More than 3 |

TABLE 17-continued

Questionnaire survey

| | | | | | | |
|---|---|---|---|---|---|---|
| 24. | What did you think of the texture of the chewing gum? | Much too soft | A little too soft | Just right | A little too hard | Much too hard |
| 25. | What did you think of the flavour of the chewing gum? | Much too sweet | A little too sweet | Just right | A little too sour | Much too sour |
| 26. | What did you think of the moisture of the chewing gum? | Much too dry | A little too dry | Just right | A little too moist | Much too moist |
| 27. | What did you think of the size of the chewing gum? | Much too small | A little too small | Just right | A little too big | Much too big |

The invention claimed is:

1. A chewing gum composition, wherein the chewing gum composition comprises gum base,
wherein the chewing gum composition comprises 0.0 to 1.5% by weight of flavor ingredients,
wherein the chewing gum composition is free of high intensity sweetener,
wherein the chewing gum composition comprises from 60 to 80% by weight of gum base,
wherein the chewing gum composition comprises from 5 to 40% by weight of polyols, the polyols consisting of mannitol,
wherein the chewing gum composition comprises one or more softeners; and
wherein the chewing gum composition induces more than 10% increase in salivary flow (g/ml) compared to unstimulated saliva flow.

2. The chewing gum composition according to claim 1, wherein the chewing gum composition decreases viscosity of the saliva in the oral cavity compared to unstimulated saliva.

3. The chewing gum composition according to claim 1, wherein said chewing gum composition comprises more than 75% by weight of gum base or more than 79% by weight of gum base.

4. The chewing gum composition according to claim 1, wherein said chewing gum composition comprises less than 0.5% by weight of flavour ingredients or less than 0.2% by weight of flavour ingredients or less than 0.1% by weight of flavour ingredients.

5. The chewing gum composition according to claim 1, wherein said chewing gum composition comprises one softener or two softeners.

6. The chewing gum composition according to claim 1, wherein the one or more softeners comprise one or more fats.

7. The chewing gum composition according to claim 6, wherein the one or more fats comprise a low melting vegetable hydrogenated fat with melting point between 35-45° C.

8. The chewing gum composition according to claim 5, wherein said softeners are lecithin and/or triacetine.

9. The chewing gum composition according to claim 8, wherein said lecithin softener is present in the amount of from 2 to 4% weight of the chewing gum composition and where said triacetine softener is present in the amount of from 2 to 4% weight of the chewing gum composition.

10. The chewing gum composition according to claim 1, wherein the one or more softeners comprise an amount of fat in the range of 0 to 30%, 1.5 to 30%, 2 to 10%, 5 to 10%, 8 to 9%, 2 to 5%, or 2 to 3% by weight of the chewing gum composition.

11. The chewing gum composition according to claim 1, wherein a film coating is applied to said chewing gum composition.

12. The chewing gum composition according to claim 1, wherein said chewing gum composition is extruded or cast into any desirable shape creating a piece of gum.

13. The chewing gum composition according to claim 12, wherein said chewing gum composition has the weight of from 0.5 to 1.5 gram per piece of gum, from 0.7 to 1.2 gram per piece of gum, from 0.45 to 0.8 gram per piece of gum, or from 0.5 to 0.7 gram per piece of gum.

14. The chewing gum composition according to claim 1, wherein said chewing gum composition comprises an anti-fungal agent.

15. The chewing gum composition according to claim 1, wherein said chewing gum composition comprises a fluoride compound.

16. The chewing gum composition according to claim 1, wherein said chewing gum composition comprises an inorganic mineral filler in the amount of less than 25%, or less than 20%, or less than 10%, or less than 5% by weight of the chewing gum composition.

17. The chewing gum composition according to claim 1, wherein said chewing gum composition comprises calcium carbonate in the amount of less than 25%, or less than 20%, or less than 10%, or less than 5% by weight of the chewing gum composition.

18. The chewing gum composition according to claim 1, wherein said chewing gum composition comprises an acidulant in the amount of less than 0.5% by weight of the chewing gum composition.

19. The chewing gum composition according to claim 1, wherein said chewing gum composition is a non-medical chewing gum composition which does not comprise an active medical ingredient or a therapeutic agent.

20. The chewing gum composition according to claim 1, wherein said chewing gum composition comprises glycerol in the range of 1 to 4% by weight of the chewing gum composition.

21. The chewing gum composition according to claim 1, wherein the chewing gum composition induces decreased viscosity of the saliva in the oral cavity compared to unstimulated saliva.

22. The chewing gum composition according to claim 1, wherein no coating is applied to said chewing gum composition.

* * * * *